United States Patent
Henry et al.

(10) Patent No.: US 9,968,602 B2
(45) Date of Patent: May 15, 2018

(54) MODULATION OF CELL FATES AND ACTIVITIES BY PHTHALAZINEDIONES

(71) Applicant: Bach Pharma, Inc., North Andover, MA (US)

(72) Inventors: Mark O. Henry, North Andover, MA (US); William S. Lynn, Hillsborough, NC (US)

(73) Assignee: BACH PHARMA, INC., North Andover, MA (US)

( * ) Notice: Subject to any disclaimer, the term of this patent is extended or adjusted under 35 U.S.C. 154(b) by 309 days.

(21) Appl. No.: 13/764,365

(22) Filed: Feb. 11, 2013

(65) Prior Publication Data

US 2014/0030317 A1  Jan. 30, 2014

Related U.S. Application Data

(60) Continuation of application No. 13/537,900, filed on Jun. 29, 2012, now abandoned, which is a continuation of application No. 13/294,634, filed on Nov. 11, 2011, now abandoned, which is a continuation of application No. 13/074,784, filed on Mar. 29, 2011, now abandoned, which is a continuation of application No. 12/044,716, filed on Mar. 7, 2008, now abandoned, which is a continuation of application No. 11/699,853, filed on Jan. 30, 2007, now abandoned, which is a division of application No. 11/199,394, filed on Aug. 8, 2005, now Pat. No. 7,326,690, which is a continuation-in-part of application No. 10/283,647, filed on Oct. 30, 2002, now Pat. No. 6,953,799.

(51) Int. Cl.
| | | |
|---|---|---|
| *A61K 38/06* | (2006.01) |
| *A61K 31/502* | (2006.01) |
| *A61K 31/573* | (2006.01) |
| *A61K 38/44* | (2006.01) |
| *A61K 31/197* | (2006.01) |
| *A61K 31/65* | (2006.01) |
| *A61K 31/519* | (2006.01) |
| *A61N 5/10* | (2006.01) |
| *A61K 31/56* | (2006.01) |
| *A61K 31/50* | (2006.01) |
| *A61K 31/385* | (2006.01) |
| *A61K 31/195* | (2006.01) |

(52) U.S. Cl.
CPC .......... *A61K 31/502* (2013.01); *A61K 31/197* (2013.01); *A61K 31/519* (2013.01); *A61K 31/573* (2013.01); *A61K 31/65* (2013.01); *A61K 38/44* (2013.01); *A61N 5/10* (2013.01)

(58) Field of Classification Search
CPC ........ A61K 38/00; A61K 31/57; A61K 31/50; A61K 31/385; A61K 31/195
USPC .................. 514/18, 171, 248, 440, 562, 21.9
See application file for complete search history.

(56) References Cited

U.S. PATENT DOCUMENTS

| | | | | |
|---|---|---|---|---|
| 5,543,410 A * | 8/1996 | Minin | .................. | C07D 237/32 514/248 |
| 5,874,444 A * | 2/1999 | West | ...................... | A61K 31/00 514/249 |
| 6,337,065 B1 * | 1/2002 | Jacobson | ............. | A61K 8/4926 424/401 |

OTHER PUBLICATIONS

The Merck Index, 11th edition, published 1989 by Merck & Inc., (NJ), pp. 463, 464 and 1224.*
The Merck Manual of Diagnosis and Therapy, published 1982 by Merck, Sharp & Dohme, (NJ), pp. 262-265 and 1190-1193.*

* cited by examiner

*Primary Examiner* — Raymond J Henley, III
(74) *Attorney, Agent, or Firm* — Ann-Louise Kerner, Esq.; Morse, Barnes-Brown & Pendleton, P.C.

(57) ABSTRACT

Phthalazinediones that function as intracellular redox modulators are useful in treating cells in various disease states where intracellular redox status is impaired. By buffering aberrant redox states, phthalazinediones enable cellular processes essential for survival and augment medical treatments. The phthalazinediones of the invention can modulate functions related to cell growth, differentiation, activity, or death, to correct aberrations and restore homeostasis, and can serve as adjunctive therapy in treating various disease conditions.

7 Claims, No Drawings

MODULATION OF CELL FATES AND ACTIVITIES BY PHTHALAZINEDIONES

This application is a continuation of application Ser. No. 13/537,900 filed Jun. 29, 2012, now abandoned, which is a continuation of application Ser. No. 13/294,634 filed Nov. 11, 2011, now abandoned, which is a continuation of application Ser. No. 13/074,784 filed Mar. 29, 2011, now abandoned, which is a continuation of application Ser. No. 12/044,716 filed Mar. 7, 2008, now abandoned, which is a continuation of application Ser. No. 11/699,853 filed Jan. 30, 2007, now abandoned, which is a division of application Ser. No. 11/199,394 filed Aug. 8, 2005, now U.S. Pat. No. 7,326,690, which is a continuation-in-part of application Ser. No. 10/283,647 filed Oct. 30, 2002, now U.S. Pat. No. 6,953,799. The entire contents of each of the above documents are herein incorporated by reference in their entirety.

BACKGROUND OF THE INVENTION

Current medical treatments generally focus on the disease and strive to eliminate the inciting agent or the symptoms, often injuring healthy tissue in the process. The present invention focuses instead on the patient, to enable self-repair mechanisms by supporting the patient's body in controlling or stabilizing its cellular functions without toxic side effects. The methods and compositions of the invention comprise phthalazinedione compounds that buffer intracellular reduction and oxidation (redox) reactions and thereby modulate cellular functions of growth, differentiation, activity, and death in various disease states.

In healthy cells, a balance of redox reactions maintains a physiologically appropriate environment for various cellular functions related to growth, differentiation, activity, and death. The proper coordination of such functions ensures homeostasis and the health of cells. Research has shown that alterations in cellular redox status affect activities such as cellular signaling, suggesting that altering the cellular redox status could also affect cellular activation, which results from certain cellular signals (U.S. Pat. No. 5,994,402). Altering the intracellular redox state by depleting cells glutathione (GSH), an endogenous "redox agent," has also been shown to protect cells from certain injury and to promote their survival (U.S. Pat. No. 5,994,402), again suggesting a link between alterations in the cellular redox state and cellular functions.

Stresses that perturb a cell's redox status may be internal or external. For example, a genetic mutation may produce defective protein products that function abnormally or not at all. These defective proteins could disrupt certain cellular processes, including redox reactions. Cellular redox reactions may also be disrupted by microbes, toxins, allergens, or other agents external to the cell. The external stress could trigger defensive responses that leave the cell's redox system depleted and unstable.

An imbalanced redox state, even if not the cause of a particular disease condition, may facilitate that condition by providing an "unhealthy" environment in which necessary cellular functions become impaired. Cellular redox status may become impaired in numerous disease conditions. Under the stress of a disease state, the rate of redox reactions increases or decreases as needed by the cell. Significant or prolonged deviations in the intracellular redox status disable cellular processes, including defense mechanisms. When such cellular functions are impaired, the survival of the cell becomes uncertain. Maintenance of the proper redox status is thus critical to the fate of the cell.

To counter and correct disturbances in the redox status, cells require agents that can modulate redox imbalances, to facilitate reduction or oxidation reactions as appropriate. Agents currently available for correcting redox imbalances are inadequate in that they are labile, quickly oxidized, or unable to translocate to the proper region of the cell. Examples of such exogenous redox agents include cysteine, reduced lipoates or thiols, glucocorticoids, and other antioxidants. Redox agents that remain stable, active, and functional in the cellular environment are necessary.

Although their role in modulating intracellular redox status was not recognized, phthaloylhydrazide, phthalazinedione, and phthalazine derivatives have been described as having anti-inflammatory, anti-cancer, and anti-hypoxic effects (U.S. Pat. Nos. 6,686,347; 6,489,326; 5,874,444; 5,543,410; 5,512,573; 4,250,180). However, toxicity and the lack of pharmacological activity of certain phthaloylhydrazides, including 2,3-dihydrophtbaluzine-1,4-dione and 5-amino-2,3-dihydrophthalazine-1,4-dione, were noted (U.S. Pat. Nos. 6,489,326; 5,543,410; 5,512,573). Luminol, also known as o-aminophthaloylhydrazide, 3-aminophthalhydrazide, 5-aminophthaloylhydrazide, or 5-amino-2,3-dihydro-1,4-phthalazinedione, was considered toxic and used in photothermographic imaging, chemiluminescent assays and labeling of cellular structures, detection of copper, iron, peroxides, or cyanides, and forensic science to detect traces of blood (U.S. Pat. Nos. 5,279,940; 4,729,950; Merck Index, 13th ed, (2001), monograph no. 5622).

Nonetheless, the compound 5-aminophthaloylhydrazide was identified for use in treating inflammatory conditions such as ulcerative colitis, Crohn's disease, diffuse sclerosis, diarrhea, proctitis, hemorrhoids, anal fissures, dyspepsia, intestinal infection, Alzheimer's disease, osteoarthritis, macular degeneration, and proctosigmoiditis (U.S. Pat. Nos. 5,874,444; 5,543,410; EP 617024; RU2211036), as well as for use in treating psoriasis, infarct, and transplant rejection (U.S. Pat. Nos. 6,489,326; 5,512,573). Other phthaloylhydrazide derivatives identified as having pharmacological activity include 2,3-dihydroplithalazine-1,4-dione, 2-amino-1,2,3,4-tetrahydrophthalazine-1,4-dione sodium salt dihydrate, 4-aminophthaloylhydrazide, 4,5-aminophthaloylhydrazide, and 4,5-methylaminophthaloylhydrazide (U.S. Pat. Nos. 6,489,326; 5,512,573; RU 2113222).

Phthalazinedione compounds, including luminol, have also been described as an inhibitor of poly (ADP-ribose) polymerase, an enzyme that responds to DNA damage (U.S. Pat. Nos. 5,874,444; 5,719,151; 5,633,282), and for treating conditions involving the functions of poly (ADP-ribose) polymerase (U.S. Pat. Nos. 5,874,444; 5,719,151; 5,633,282). A method of manufacturing the sodium salt of 5-amino-2,3-dihydrophthalazine-1,4-dione and its pharmaceutical use for immunomodulation, inflammation, and antioxidant treatment have been described (U.S. Pat. No. 6,489,326; RU 2222327).

SUMMARY OF THE INVENTION

Phthalazinediones of the invention may be used to modulate redox imbalances and to support a patient's body in a variety of disease states and in treating metabolic distress, inflammation, infectious conditions, neurological disorders, immune disorders, proliferative diseases, and senescence. The phthalazinediones may also be used in conjunction with standard treatment methods such as chemotherapy, radiation, nutrition, pharmaceutical treatment, and surgery.

DETAILED DESCRIPTION

The present invention describes the use of phthalazinedione compounds in treating diseases or disorders involving impaired or aberrant intracellular redox states. By buffering redox imbalances, phthalazinediones can reversibly and selectively modulate cellular functions, e.g., upregulating mitochondrial aerobic metabolism when a cell under stress needs energy for defense or repair, or downregulating metabolism when the stressed cell is overactive. Phthalazinediones can modulate cellular processes such as proliferation, secretion, differentiation, transformation, migration, and apoptosis, without toxic side effects on healthy cells.

Under any stress, intracellular redox status is inevitably impaired as aerobic metabolism is necessarily overworked. Any stress to the cell, especially if prolonged, will deplete the cell of endogenous redox agents, including thiols, glutathione, thioredoxins, iron-sulfur proteins, cysteine, and thiol proteins, as well as redox-sensitive proteins such as catalase. Chronic stress leads to cellular and organelle thiol deficiencies, as blood cysteine is limited. In turn, since many cellular pathways are controlled by or depend on intracellular redox activities, thiol deficiencies lead rapidly to impaired energy production, with increased oxidant production and progressive mitochondrial and cell death.

In mitochondrial aerobic metabolism, electron flow is fragile and easily perturbed by oxidant stresses. Under stress, the cell must rapidly increase both the electron flow and the subsequent membrane proton ($H^+$) gradient. However, electron flow and proton gradient may fail if overactivated or stressed. Electrons are then diverted directly to oxygen ($O_2$), producing toxic superoxide ($O_2^-$), while the proton gradient declines, hindering ATP production. Moreover, under oxidant stress, mitochondrial membrane channels and permeability pores become oxidized, which distorts the channels and opens the pores. Consequently, protons, substrate anions, glutamate, reductants, cytochrome c, and nucleotides all leak through the distorted channels and opened pores, leaving the mitochondrion and cell deficient in essential substances, energy, and redox status.

With prolonged thiol deficiencies, replacement therapy with available thiols is difficult and usually inadequate. Cysteine and other reduced thiols are labile and rapidly oxidized to toxic metabolites in the presence of oxygen. Most antioxidants, which dissipate oxygen-based oxidants, are unable to penetrate to the electron-transporting inner mitochondrial membrane to modulate the iron-sulfur protein mediated electron flow in mitochondrial Complex III or to stabilize disulfide cross-linkages that control permeability of the mitochondrial megapores and channels. Antioxidants also cannot supply the cysteine required in the manufacture of most proteins or the energy required to combat chronic stresses or repair cellular damages.

In general, a therapeutically effective amount of a phthalazinedione of the invention that is sufficient to ameliorate disease symptoms will depend on the acuteness of the disease, the particular redox status or deficiency of the patient, the developmental condition of the stressed cell, and also the state of oxidation of the phthalazinedione, but will be in the range of about 0.01-100.0 mg per kg of body weight or about 1.0-10,000 mg per day, e.g., administered in amounts of 1.0, 10.0, 50.0, 100.0, 200.0, 300.0, 400.0, 500.0, 600.0, 700.0, 800.0, 900.0, 1000.0, 2000.0, 3000.0, 4000.0, 5000.0, 6000.0, 7000.0, 8000.0, 9000.0, or 10,000.0 mg.

The phthalazinedione compounds of the present invention are preferably incorporated into pharmaceutical forms suitable for administration by oral, nasal, mucosal, vaginal, rectal, transdermal, or parenteral routes, including subcutaneous, intramuscular, intravenous, and intraperitoneal, e.g., tablet, capsule, granule, powder, solution, suspension, microsphere, liposome, colloid, lyophilized composition, gel, lotion, ointment, cream, spray, and suppository, and preferably include pharmaceutically acceptable excipients, carriers, adjuvants, diluents, or stabilizers as is well known to the skilled in the art.

The phthalazinedione may be a derivative compound containing a substituent that enhances the activity, stability, or other property of the compound. Such a derivative compound may be an amino phthalazinedione or a phthalazinedione comprising a haloamino, alkylamino, acylamino, alkanolamino, alkenylamino, alkoxyamino, haloalkylamino, allylamino, or sulfhydrylamino (thiolamino or mercaptoamino) group or other substituents that confer a preferred function on the compound. Furthermore, the phthalazinedione may be a bromoamino, chloroamino, fluoroamino, iodoamine, methylamino, ethylamino, propylamino, isopropylamino, methanoylamino (formylamino), ethanoylamino (acetylamino), propanoylamino, hydroxyamino, carboxylamino, methanolamino, ethanolamino, propanolamino, methenylamino, ethenylamino, propenylamino, methoxyamino, ethoxyamino, propoxyamino, or dimethylamino derivative.

Examples of such phthalazinedione derivatives include, but are not limited to, 5-amino-2,3-dihydrophthalazine-1,4-dione (luminol), 6-amino-2,3-dihydrophthalazine-1,4-dione (isoluminol), 5-amino-2,3-dihydrophthalazine-1,4-dion-8-yl (luminyl), N-bromo-5-amino-2,3-dihydroptithalazine-1,4-dione, N-chloro-5-amino-2,3-dihydroplithalazine-1,4-dione, N-fluoro-5-amino-2,3-dihydrophthalazine-1,4-dione, N-iodo-5-amino-2,3-dihydrophthalazine-1,4-dione, N-methyl-5-amino-2,3-dihydrophthalazine-1,4-dione, N-ethyl-5-amino-2,3-dihydrophthalazine-1,4-dione, N-propyl-5-amino-2,3-dihydrophthalazine-1,4-dione, N-isopropyl-5-amino-2,3-dihydrophthalazine-1,4-dione, N-methanoyl-5-amino-2,3-dihydrophthalazine-1,4-dione, N-ethanoyl-5-amino-2,3-dihydrophthalazine-1,4-dione, N-propanoyl-5-amino-2,3-dihydrophthalazine-1,4-dione, N-hydroxyl-5-amino-2,3-dihydrophthalazine-1,4-dione, N-carboxyl-5-amino-2,3-dihydrophthalazine-1,4-dione, N-methanol-5-amino-2,3-dihydrophthalazine-1,4-dione, N-ethanol-5-amino-2,3-dihydrophthalazine-1,4-dione, N-propanol-5-amino-2,3-dihydroplithalazine-1,4-dione, N-methenyl-5-amino-2,3-dihydrophthalazine-1,4-dione, N-ethenyl-5-amino-2,3-dihydrophthalazine-1,4-dione, N-propenyl-5-amino-2,3-dihydroplithalazine-1,4-dione, N-methoxy-5-amino-2,3-dihydrophthalazine-1,4-dione, N-ethoxy-5-amino-2,3-dihydrophthalazine-1,4-dione, N-propoxy-5-amino-2,3-dihydrophthalazine-1,4-dione, N,N-dimethyl-5-amino-2,3-dihydrophthalazine-1,4-dione, N-acetylcysteine-5-amino-2,3-dihydrophthalazine-1,4-dione, and N-acetylglutathione-5-amino-2,3-dihydrophthalazine-1,4-dione. Enantiomers, isomers, tautomers, esters, amides, salts, solvates, hydrates, analogues, metabolites, free bases, or prodrugs of the phthalazinedione or its derivative are also contemplated by the invention.

In an embodiment of the invention, phthalazinediones can be used to either facilitate or inhibit electron flow in mitochondria, and thus control ATP production. For example, in vitro, at the low dose of 20-50 μM, amino phthalazinediones facilitate electron flow at mitochondrial Complex III, thereby increasing ATP production, DNA synthesis, and cell cycling, for cell growth. At an intermediate dose of 100 μM, amino phthalazinediones slow down electron flow, with concomitant effects on ATP production, DNA synthesis, and cell cycling, so that differentiation can proceed. At the high dose of 200 μM, amino phthalazinediones completely stop ATP production, DNA synthesis, and cell cycling in the stressed cell, such that the cell becomes quiescent but does not die.

Thus, phthalazinediones of the invention may be used to control cell fates and serve as redox buffers for the redox- and thiol-sensitive energy producing pathways in the mitochondrion, signaling pathways at the cell plasma membrane, and glutamate uptake and cytokine secretion by astrocytes in the central nervous system (Trott et al., *J. Biol. Chem.* 271: 5976-5979, 1996). In particular, amino phthalazinediones catalyze disulfide cross-linkages in the adenine nucleotide translocase (ANT) of the mitochondrial anion channels and in the megapores, which prevents energy production, increases production of the potent signal transducers hydrogen peroxide ($H_2O_2$) and superoxide ($O_2^-$) (Zamzami et al., *Oncogene* 16: 1055-1063, 1998; Constantini et al., *J. Biol. Chem.* 271: 6746-6751, 1996), and liberates the apoptosis-inducing factors cytochrome c and AIF.

Under certain conditions, loss of redox control may cause:

(1) cross-linking of thiols in the adenine nucleotide translocase and other proteins, which then opens the mitochondrial transmembrane pores and channels and leads to a decline in mitochondrial voltage and energy production (Constantini et al., *J. Biol. Chem.* 271: 6746-6751, 1996; Larochette et al., *Exp. Cell Res.* 249: 413-421, 1999; Zamzami et al., *Oncogene* 16: 1055, 1998);

(2) increases in intracellular calcium levels;

(3) activation of redox defenses and heat shock proteins;

(4) activation of redox-sensitive cell cycling factor AP-1 and E2F/Rb, pathway;

(5) activation of apoptotic pathways via AsK-1, with liberation of caspases, cytochrome c, and AIF from the failing mitochondrion;

(6) a decline in ADP-dependent electron flow, as well as alteration of mobility of redox sensitive iron-sulfur proteins at mitochondrial Complex III (Zhang et al., *Biol. Chem.* 275: 7656-7662, 2000);

(7) oxidation of macromolecules, including redox-sensitive proteins such as glutamate transporters (Trotti et al., *J. Biol. Chem.* 271: 5976-5979, 1996), mitochondrial DNA, and membrane lipids;

(8) a failure in modulation of redox-sensitive phosphatases PTB-1, SHP-1, and SHP-2 (Doza et al., *Oncogene* 17: 19-26, 1998); and (9) dysregulation of the thiol-sensitive MAP kinase-Ras pathway, which controls cellular proliferation.

With redox support to buffer the redox stress and restore the redox status, the mitochondrion resumes energy production. The cell then repairs stress-induced damages, restocks essential substrates, and removes all offenders, in essence treating its own disease. To be successful, any exogenous redox agent must therefore enable the cell to correct the redox aberration, remove the cellular stress, and repair mechanical damages, without toxic side effects. Accordingly, in an embodiment of the invention, phthalazinediones primarily support metabolically distressed cells in a subject, by buffering the intracellular redox status without toxic side effects, to enable the subject's cellular repair or defense functions, rather than treat a particular condition in terms of trying to eliminate the disease or its cause.

Redox support therapy may be utilized in various disease states, as in:

(1) conditions of metabolic distress, such as redox imbalance or deficiency, metabolic syndrome (Syndrome X), intoxication, diabetes, insulin resistance, hyperglycemia, hypoglycemia, hyperinsulinemia, hypoinsulinemia, hypoadiponectinemia, hyper fatty academia, inflammation, tissue injury, and burns;

(2) inflammatory conditions where overactive cells, e.g., lymphocytes, macrophages, astrocytes, or microglia, strain redox defenses and energy production, such as Parkinson's disease, Alzheimer's disease, Huntington's disease, multiple sclerosis (MS), Guillain-Barré syndrome (GBS, acute inflammatory demyelinating polyneuropathy, acute idiopathic polyradiculneuritis, acute idiopathic polyneuritis, or Landry's ascending paralysis), Lyme disease, Crohn's disease, ulcer, colitis, hemorrhoids, diarrhea, proctitis, arthritis, osteoarthritis, rheumatoid arthritis, stroke, myocardial infarction, auricular or atrial fibrillation, preexcitation syndrome (Wolff-Parkinson-White syndrome), arteriosclerosis, atherosclerosis, inflammation of blood vessels that characterize vascular disease in heart and brain, thromboangiitis obliterans (Winiwarter-Buerger disease), other inflammatory conditions of the vascular system, inflammatory conditions of the skin such as dermatitis, eczema, psoriasis, postoperative complications, peritonitis, bronchitis, and pleurisy;

(3) infectious conditions such as HIV infection, acquired immunodeficiency disease (AIDS), hepatitis, herpes, Lyme disease, toxic shock syndrome, dysentery, erysipelas, hantavirus pulmonary syndrome, respiratory syndromes such as pneumonia and tuberculosis, and other viral or bacterial related conditions or diseases;

(4) neurological disorders such as Alzheimer's disease, Parkinson's disease, Huntington's disease, Cockayne syndrome, amyotrophic lateral sclerosis (ALS or Lou Gehrig's disease), MS, Bloom's disease, dementia, dystonia, Charcot-Marie-Tooth syndrome (CMT), Dejerine-Sottas syndrome, Roussy-Levy syndrome, Rosenberg Chutorian syndrome, Korsakoff syndrome, Friedreich ataxia, Machado-Joseph disorder, progressive supranuclear palsy (PSP or Steele-Richardson-Olszewski syndrome), GBS, neurally mediated hypotension, pain syndromes such as fibromyalgia, reflex sympathetic dystrophy syndrome (RSDS or complex regional pain syndrome, CRPS), myofascial pain syndrome (MPS), patellofemoral pain syndrome, and other neurodegenerative conditions;

(5) immune disorders, including multiple chemical sensitivity syndrome (MCS), leukemia, GBS, immune deficiency diseases such as AIDS, transplant or graft rejection as in graft-vs-host disease, allergies or allergic reactions, sinusitis or sinus conditions, eczema, psoriasis, asthma, autoimmune diseases or disorders such as systemic lupus erythematosus, scleroderma, and rheumatoid arthritis, Wegener's granulomatosis, diabetes mellitus, Crohn's disease, and Wiskott-Aldrich syndrome;

(6) proliferative diseases, such as cancer, including leukemia, lymphoma, and myeloma, tumors, melanoma, carcinoma, sarcoma, prostatic hypertrophy or adenoma, atherosclerosis, angiogenesis, restenosis, proliferative diseases of the vascular system or endometrium, and other syndromes of rapid cell proliferation or clonal expansion; and (7) senescence, such as that linked to or caused by genetic abnormalities as in Down syndrome, trichothiodystrophy, ataxia telangiectasia (AT), Bloom's disease, xeroderma pigmentosum, and p53 overactivity, and other premature aging or wasting diseases such as muscular dystrophy, age-related macular degeneration (AMD), metabolic syndrome, and aging.

To survive any stress, cells must replace depleted thiols and maintain optimum mitochondrial redox potentials and activities. In one embodiment of the invention, therapy includes combined treatment with phthalazinediones and compounds to replace the lost thiols, oxidatively protect the phthalazinedione, eliminate the source of stress, or otherwise support the subject in fighting a particular condition. A compound that is an amino acid, antibiotic, antiviral agent, antiinflammatory agent, antioxidant, immunomodulator, reductant, oxidative protector, steroid, or vitamin may be beneficial. Compounds such as a cysteine (e.g., acetyl cysteine, N-acetylcysteineamide), glutathione, lipoic acid (e.g., alpha lipoic acid, dehydrolipoic acid), hydralazine, thioredoxin, biopterin (e.g., tetrahydropterin, sepiapterin), glucocorticoid, dexamethasone, rasagiline, ferulic acid, minocyline, menadione, tetracycline, isosorbate dinitrate, dextromethorphan, or mixtures thereof may be used. The additional compound may be administered simultaneously, separately, or sequentially.

The preferred active ingredients may be formulated into a pharmaceutical composition with one or more pharmaceutically acceptable excipients. For example, a pharmaceutical composition may comprise a phthalazinedione, a glutathione, and one or more pharmaceutically acceptable excipients. The pharmaceutical composition may be in the form of a tablet, capsule, granule, powder, solution, suspension, microsphere, liposome, colloid, lyophilized composition, gel, lotion, ointment, cream, spray, or suppository and administered intravenously, intramuscularly, intraperitoneally, subcutaneously, orally, nasally, mucosally, transdermally, parenterally, vaginally, or rectally. A therapeutically effective amount of the phthalazinedione or a pharmaceutical composition comprising a therapeutically effective amount of the phthalazinedione is administered to a subject in metabolic distress, to maintain the desired redox status and mitochondrial energy production, as well as the redox-sensitive MAP kinase-Ras PT3K signal transduction pathways.

The amount of phthalazinedione needed or effective at any one point is cell- and stress-dependent. Optimum dosage and treatment require proper diagnosis of the thiol redox status of the patient's aerobic metabolism in the stressed mitochondria. Administration sufficiently early on in cell or stress development, such that cellular structures or functions have not deteriorated beyond repair, e.g., mitochondria swollen and leaky, cells entering apoptosis, would be particularly beneficial. The thiol redox status must also be frequently monitored, since phthalazinediones can be oxidatively very labile and rapidly expended.

In tissue culture, small doses of less than 1 µg/ml of an amino phthalazinedione are effective for conditions with chronic losses of cells, especially of stem or developing cells, as in neuroimmunodegenerative syndromes. In conditions where proliferation and apoptotic rates are out of control, including cancer, autoimmunity, infection, and traumas, doses greater than 50 µg/ml of amino phthalazinediones are required. Successful treatment with the phthalazinedione compounds of the invention therefore depends both on redox diagnosis with repeated assessment of cellular thiol redox status and on maintenance of proper dosage of the phthalazinedione over time. Treatment with phthalazinediones is directed at cells or organs in which stress has dysregulated thiol redox homeostasis, with resulting energy deprivation and oxidant stress.

In one embodiment of the invention, amino phthalazinediones also act as efficient substrates for reaction with many of the reactive oxygen species and radicals that are inevitably generated in the stressed mitochondrion. Because of their antioxidant, anti-inflammatory, antiproliferative, immunomodulatory, redox-buffering, and non-toxic properties, phthalazinediones can be beneficial as adjunctive support therapy for the stressed cell regardless of the compromising stress or its downstream symptoms. In rare disease states, redox support may be sufficient for the diseased cell to treat itself, but in some situations, the cell will also need the mechanical, pharmacological, or genetic support of standard medical treatments such as radiation, chemotherapy, laser therapy, surgery, medication, and nutrition used in treating particular disease conditions. As adjunct support therapy, the phthalazinediones of the invention may be administered simultaneously, separately, or sequentially for a combined treatment regimen. The following examples further illustrate the invention.

Example 1

Uncontrolled Inflammation

In inflammatory conditions, such as acute infections, wounds, and immune responses, phthalazinediones, especially amino phthalazinediones, quickly ameliorate the painful redox-induced edematous swelling and facilitate rapid healing. Edematous inflammatory lesions in intestines, such as duodenal ulcers, ulcerative colitis, and acute vascular injury, are all suppressed to some degree by thiol redox modulators, including dihydrolipoates, reduced biopterins, amino phthalazinediones, and more slowly by glucocorticoids. Healing rates increase, with replacement of the injured epithelial cells by thiol redox-stimulated new cell growth. Thus, phthalazinediones, acting as thiol redox modulators, suppress injurious over-reactive inflammatory responses and also facilitate healing and replacement of injured cells.

Example 2

Uncontrolled Proteolysis

In conditions with aberrant or uncontrolled proteolysis, as in apoptosis or necrosis, thiol redox modulators, especially thioredoxin, either upregulate or downregulate the regulatory proteases involved in processing and digesting the thiol redox dependent caspases, endonucleases, and histone deacetylases responsible for protein and DNA hydrolysis. Diamide, a phthalazinedione with activity similar to the oxidized 4-amino phthalazinedione, can activate and cross-link proteases that hydrolyze procaspase 3 to the active caspase fragments that, along with cytochrome c, initiate the apoptotic cascade in the nucleus.

Since these cross-linking agents can also oxidize essential membrane proteins, such as the adenine nucleotide translocase in mitochondria or amyloid protein fragments in brain, the result is membrane pore formation in mitochondria with increased reactive oxygen species and cell destruction (Ueda et al., *J. Immunol*, 161: 6689-6695, 1998). Thus, reduced phthalazinediones can up- or down-regulate redox-sensitive proteases and thereby dictate life and death of stressed proliferating cells.

Example 3

Helicase Deficiencies

The XPD gene of the xeroderma pigmentosum family codes for a helicase. In XPD deficiency, DNA transcription and repair functions are impaired, resulting in multiple symptoms of early aging (De Boer et al., *Science* 296:

1276-1281, 2002), Wasting, loss of subcutaneous fat and muscle cells, gray brittle greasy hair with hyperplasia of sebaceous and mammary glands, severe osteoporosis, atrophic germ and stem cells, and immunodegenerative and hyperplastic changes all occur prematurely in XPD-deficient mice or humans.

The failure to maintain normal numbers of cells or normal amounts of cellular thiols, at least in the brittle hair, suggests that a global thiol redox deficiency is responsible for the progressive wasting and chronic cell losses. Since amino derivative phthalazinediones with reduced thiol redox modulators, at low dosage, stimulate cell growth and maintain thiol redox status in cells, treatment with appropriate amounts of reduced thiol redox modulators combined with the phthalazinediones of the present invention will likely prevent the premature aging in regulatory gene deficiencies such as XPD deficiency.

Example 4 p53 and Aging

In conditions where cell growth and tumor formation are constantly suppressed by growth suppressor genes like p53, signs of premature aging and replication senescence appear early (Tyner et al., *Nature* 415: 45-50, 2002). Chronic cell losses in skin, hair, bone, adipose tissue, and the immune system occur. The p53 protein is a potent transcription factor that suppresses cell growth and DNA synthesis and is also an activator of genes that induce oxidative stress and apoptosis, such as Bax and caspases 3 and 9.

Thiol redox modulators such as phthalazinediones, which maintain cellular replication pathways by modulating cellular redox status, override the p53-induced suppression and maintain a balance between apoptotic or proliferation pathways, depending on dosage. Data to support this homeostatic concept for thiol redox modulators in p53-induced aging are under evaluation. Since thiol redox modulators beneficially balance rates of cell death and proliferation in other syndromes of premature aging, including XPD deficiency and retrovirus-induced degenerative diseases, it is likely that thiol redox modulators, at appropriate dosages, can re-balance the p53-induced thiol redox potential and thereby prevent the degenerative sequelae.

Example 5

Retroviral-Induced Redox Imbalance

Oncogenic retroviral infections such as HIV in humans or MOMU-LV-Ts1 in mice cause degenerative changes with severe losses of brain cells, immune cells, and germ cells. Other cells like astrocytes and microglia in brain become activated, secrete nitric oxide (NO) and superoxide ($O_2^-$), and grow and accumulate excessively. This imbalance in cell growth and death rates eventually leads to fatal immune and neuronal deficiency syndromes with subsequent transformation in some cells.

In mice infected at 2 days of age with the Ts1 virus, hind limb paralysis occurs with severe wasting, especially of immune organs. In humans infected with HIV, severe immune deficiency with sensory and motor neuropathy also results. In these wasting syndromes with disordered life and death pathways in various cells, some therapeutic attempts with thiol redox modulators other than amino phthalazinediones have been partially successful (Lynn and Wong, *NeuroImmunomodulation* 4: 277-284, 1997; Yan et al., *FASEB J.* 15: 1132-1138, 2001). In these studies, phthalazinediones plus thiol redox modulators appear to be sufficient to maintain survival and an adequate intracellular thiol redox potential in brain and in thymus.

Since retroviruses activate caspase-dependent apoptosis, and since thiol redox modulators, oxidized and reduced, regulate caspase production from procaspases (Nobel et al., *Chem. Res. Toxicol.* 10: 636-643, 1997), thiol redox modulators in mitochondria, especially an amino phthalazinedione plus dexamethasone, will likely prevent both the loss and the hyperplasia of cells dysregulated by the viruses. Experiments using various thiol redox modulator regimens as preventative therapy in Ts1-infected mice are currently underway.

Example 6

Polyglutamine Model

In disease states where aberrant peptides slowly accumulate in the brain, early neuronal death with glial hypertrophy occurs. In Huntington's disease, polyglutamine sequences or tracts accumulate in the huntingtin protein. These tracts bind to and inhibit transcription complexes containing Sp-1 and TAFII130 coactivators. Transcription rates decrease, and dysregulated neurons slowly die, first in the caudate nucleus and later in the hippocampus.

Non-proliferating, non-replaceable neurons usually die from metabolic redox imbalances, rather than from programmed death. Therefore, neuronal death in Huntington's disease is likely to be redox-mediated and induced by activation of redox-sensitive cytokines, metalloproteases, and reactive oxygen species (ROS) by activated migroglia and astrocytes (Chen et al., *Nature Med.* 797-801, 2000). In that case, reduced thiol redox-modulators, which at low doses promote cell growth and longevity in redox-suppressed cells, should prove to be useful therapy (Dunah et al., *Science* 296: 2238-2243, 2002).

In other neurodegenerative syndromes in which aberrant peptides accumulate, including Alzheimer's and Parkinson's diseases, presenilin or synucleins may be responsible for accumulation of the Lewy bodies and β-amyloid peptides. Accumulation of these hydrophobic peptides in plasma, mitochondrial, or endoplasmic reticulum membranes of the cell may be responsible for the neuronal losses in these syndromes. These toxic peptides, like the polyglutamine proteins in Huntington's disease, also lead to astroglia-induced imbalances in thiol redox metabolism, with cell swelling, membrane leakiness, and mitochondrial necrosis. Maintenance of thiol redox status with reduced thiol redox modulators, especially an amino phthalazinedione and acetyl cysteine, should prevent or delay the neuronal death in these degenerative diseases (Wolfe and Selkoe, *Science* 296: 2156-2157, 2002; Welhofen et al., *Science* 296: 2215-2218, 2002).

Example 7

NMDA-Induced Excitotoxicity Model

In NMDA-induced neuronal excitotoxicity, secreted microglial inflammatory products—glutamate, quinolinic acid, inflammatory cytokines, tumor necrosis factor, IL-1B, superoxide ($O_2^-$), and nitric oxide (NO)—are likely responsible for the neuronal necrosis (Tikka and Kolstinabo, *J. Immunol.* 166: 7527-7533, 2001). These excitotoxins all rapidly perturb redox homeostasis in neurons, which slowly die, and in activated astroglia, which become activated and proliferate.

Minocycline, a cyclic polyhydroxy ketonic amide, which suppresses mitochondrial activity, prevents both the NMDA-induced proliferation of and toxic secretions by activated astrocytes, as well as the subsequent neuronal death (Tikka and Kolstinaho, *J. Immunol.* 166; 7527-7533, 2001). This suggests that cell death in neurons, secretory proliferative activation of astroglia, and proliferative response in astrocytes in the spinal cord are mitochondrial redox-mediated and that correction of thiol redox status by phthalazinediones should be able to control the fate of these brain cells.

Example 8

Premature Aging with Cancer Models

In regulatory gene-dependent syndromes of premature aging, including ataxia telangiectasia, Down syndrome, trichothiodystrophy, Bloom's disease, p53 over-activity (De Boer et al., *Science* 296: 1276-1281, 2002; Tyner et al., *Nature* 415: 45-50, 2002), in which life and death of specific cell types are aberrant, appropriate treatments in vitro and in vivo with thiol redox modulators have been partially successful. In ataxia telangiectasia gene (ATM) deficiency in mice, early pretreatment with dexamethasone, the glutathione secretagogue, completely prevents the excessive proliferation and development of the fatal thymic cancer.

Other thiol redox modulators, such as N-acetyl cysteine and dehydrolipoic acid, also delay the premature degeneration of cells and the thymomas. Thiol redox modulators also correct the delayed differentiation and excessive production of DNA in ATM-deficient lymphoid cells (Yan et al., *FASEB J.* 15: 1132-1138, 2001; Lynn et al., unpublished). However, in the ATM-deficient mice, treatment was fully successful only if the thiol redox modulators were applied early, before two weeks of age and before tumor development.

Dexamethasone alone completely prevents tumor formation if given to 10-day old ATM-deficient mice for three weeks, but does not suppress tumor growth or increase longevity if given at physiologic doses at three months of age. Whether amino phthalazinediones with other thiol redox modulators, which suppress growth of non-transformed ATM-deficient cells in vitro, can fully suppress tumors in vivo, without toxicity, has not been rigorously evaluated. Cross-linking redox modulators such as diamide, menadione, and oxidized phthalazines are known to stop cell growth, activate caspases, and initiate apoptosis in some tumor cells (Pias and Aw, *FASEB J.* 16: 781-790, 2002).

Example 9

Oxygen-Based Model

In acute metabolic distress, as in hypoxia, redox-sensitive transcription factors such as H1FA are rapidly activated, or under-activated if the oxygen deprivation is not too severe. These transcription factors are triggered by the alternate redox-sensitive mammalian target of rapamycin (mTOR) signal transduction pathway, which is unregulated by low oxygen, ATP, and amino acids. Activated mTOR markedly upregulates DNA synthesis and cellular proliferation, especially in endothelial and vascular smooth muscle cells. Consequently, mTOR is involved in many redox-sensitive proliferative diseases of vascular tissues, including diabetic retinopathy, psoriasis, rheumatoid arthritis, certain tumors, and arteriosclerosis (Humar, *FASEB J.* 16: 771-780, 2002).

Whether mTOR or its upstream activators are redox sensitive is not clear. Nonetheless, oxygen at low dose, like amino phthalazinediones at low dose, increases proliferation, whereas oxygen at very low dose (<1%), or phthalazines at high dose, stop proliferation and activate cell death pathways. Vascular cell fates are clearly dependent on external redox agents that modulate internal redox status, and the responses and fates of these cells are readily controlled in a dose-dependent manner by external redox agents such as oxygen, amino phthalazinedione, diamide, or permeant thiols, which modulate the mTOR-signaling pathway. These redox agents should therefore be useful as redox buffers in controlling the redox-sensitive mTOR pathway, ameliorating various vascular proliferative inflammatory diseases, and controlling angiogenesis both in tumor growth and inflammatory syndromes, particularly in brain.

Example 10

Uncontrolled Oxygen Models

In uncontrolled oxygen metabolism, oxygen is not fully reduced, such that reactive oxygen intermediates accumulate. Cell fate is highly dependent on the concentration, location, and longevity of reactive oxygen species such as $O_2^-$, $H_2O_2$, OH., NO, and $OHOO^-$. In proliferating vascular smooth muscle cells, addition of $O_2^-$ or $H_2O_2$ quickly increases DNA synthesis, via activation of the Id3/E2F pathway. In the presence of iron plus $H_2O_2$, which produces the more potent OH. radical, DNA synthesis, Id3 protein, and Id3 mRNA rapidly decline, while cell death rates increase. Thus, the fate of growing smooth muscle cells is highly dependent on oxygen redox status.

The two oxygen redox-sensitive genes, Id3 and GKLF, which are differentially responsive to oxygen redox status, are most sensitive to rapid changes in concentrations of reactive oxygen species. With increased concentrations in OH., Id3 expression is downregulated, GKLF expression is upregulated, and DNA synthesis ceases (Nickenig et al., *FASEB J.* 16: 1077-1086, 2002). The GKLF protein, when oxidized, is activated and inhibits Id3 expression by binding to the Id3 promoter. The Id3 protein, when reduced, is activated and upregulates the E2F-controlled proliferation pathway.

Thus, oxygen redox status, like thiol redox status, is a potent regulator of cell fates. Moreover, the two redox pathways, and the two electron acceptors oxygen and sulfur, interact repeatedly. For example, reduced phthalazines or thiols chemically reduce most of the reactive oxygen species, including peroxynitrite ($ONOO^-$). Tetrahydropterin ($BH_4$), a major cellular reductant in the central nervous system, reduces reactive oxygen species and the inducible oxidase iNOS. Under redox stress, in the presence of tetrahydropterin, iNOS produces nitric oxide (NO). Under redox stress when tetrahydropterin or reduced think are limited, iNOS produces superoxide ($O_2^-$). In turn, superoxide ($O_2^-$) or hydrogen peroxide ($H_2O_2$) activates Id3 and the E2F-controlled DNA synthesis pathway but only in the absence of iron or copper (Dehmer et al., *J. Neurochem.* 74: 2213-2216, 2000; Husman, et al., *FASEB J.* 10: 1135-1141, 2002; Liberatore et al., *Nature Med.* 5: 1403-1409, 1999).

Thus, intracellular redox homeostasis, whether oxygen or thiol-mediated, is dependent on concentrations of cellular reductants—tetrahydropterin, glutathione, cysteine, NADPH—and cellular oxidants—$O_2^-$, $H_2O_2$, NO, OH., $Fe^{3+}$—as well as on concentrations of permeant extracellular reductants reduced thiols, tetracyclines, phthalazines—and permeant extracellular oxidants—$O_2^-$, gamma radiation, doxorubicin, glucocorticoids, cis-platinum, doxirubicin, etc. Consequently, redox homeostasis can be readily maintained by appropriate doses of permeant redox agents, notably by phthalazinediones, and with protean therapeutic implications. Phthalazines, tetracyclines, or thiols (Tikka and Kolstinaho, *J. Immunol.* 166: 7527-7533, 2001) potentially dictate and control the cell fate in activated or stressed cells, whether the disease-inducing redox imbalance is oxygen- or sulfur-mediated. In addition to controlling proliferation and activation pathways, these redox modulators also scavenge destructive oxygen radicals and thereby prevent apoptotic and necrotic pathways.

Potential therapeutic usefulness of these redox modulators in astroglia induced neurodegenerative diseases (Tikka and Kolstinaho, *J. Immunol.* 166: 7527-7533, 2001), in renal allografts (Husman et al., *FASEB J.* 10: 1135-1141, 2002), and in inflammation-induced cell damages (Ryan et al., *Curr. Opinion in Rheumatology* 8: 238-247, 1996) are now being recognized. Thus, redox modulating compounds, especially phthalazinediones, that modulate both the oxygen and sulfur redox pathways are proving to be therapeutically useful in situations where the patient's redox mechanisms are out of control.

Example 11

Chronic Inflammation Model with Accumulation of Excess Lipids

In situations where foreign fats such as oxidized fatty acids or cholesterol accumulate, a chrome inflammatory reaction ensues. Signaling and transport processes in lipid-laden membranes falter. Lipid-laden activated macrophages accumulate. Oxidant stress follows, due to deficiency in glucose transport in the lipid-laden membranes and the increased production of oxidants and proteases by the influx of activated macrophages. Chronic localized abscesses form. In vascular tissue, atherosclerosis with occlusive diseases, stroke, myocardial infarction, cystic mastitis, wet macular degeneration, and engorged activated adipocytes are the result. In all these syndromes, thiol redox homeostasis becomes gravely perturbed and cellular redox damage occurs. Metabolic syndrome, or Syndrome X, with insulin resistance is an early sequela.

Therapies known to modulate the above lipid- and redox-induced syndromes include:

(1) thiol redox modulators, especially amino phthalazinediones, to buffer the aberrant thiol redox status;

(2) anti-proteases, especially minocycline, to block the excess proteolytic activity and suppress $O_2^-$ production by the induced NO synthase by macrophages;

(3) peroxisome proliferators, to accelerate oxidation of accumulating lipids;

(4) caloric restriction, to block input and accumulation of the aberrant lipids and $O_2^-$;

(5) glucocorticoids, to deplete thiols by excretion, inhibit growth, and accelerate death of the overactivated macrophages and microglia; and (6) sepiapterin, to prevent superoxide ($O_2^-$) production by iNOS in the brain and to prevent activation of the apoptosis stimulating kinase AsK-1 especially in the brain.

Many external therapies are therefore available to modulate and prevent the chronic abscess formations induced by accumulation of aberrant oxidized fats in cell membranes. To fully maintain optimum redox status, over time, in disease states with differing etiologies, various combinations and doses of all six redox approaches may be required. With optimum redox support, the subject will repair most damages and induce the means—for example, peroxisome proliferator receptors (PPARs) and adiponectin—to remove the offending fats. In severe defects, specific anti-proteases and antioxidants as those listed above are essential for optimal therapy.

Example 12

Redox-Controlled Neuronal Survival

Oxidizing agents such as $H_2O_2$, NMDA agonists, and N-nitrosoguanidines rapidly kill primary neurons. In the presence of oxidants the redox-sensitive nuclear poly (ADP-ribose) polymerase, which cleaves $NAD^+$ to ADP-ribose and stabilizes nuclear proteins by ADP-ribosylating them, is rapidly activated. This depletes the neuron of $NAD^+$ as well as the reductants NADH and NADPH. This also rapidly facilitates nuclear uptake of the mitochondrial redox-sensitive flavoprotein, apoptosis inducing factor (AIF).

These oxidants also open the redox-sensitive permeability transition pores and anion channels in mitochondrial membranes, which release AIF. AIF is then taken up by the poly (ADP ribose) polymerase-activated nucleus to initiate chromatin condensation. Chromatin condenses, mitochondria grow swollen, and mitochondrial processes become uncoupled. Mitochondria then produce more oxidants, $O_2^-$ and $H_2O_2$, and produce less ATP. In addition, the oxidants rapidly induce reshuffling of plasma membrane ionic phospholipids with surface exposure of phosphatidyl serine. This rapidly alters permeability and transport activities in plasma, mitochondrial, endoplasmic reticulum, and nuclear membranes. The plasma and endoplasmic reticulum membranes leak calcium, which activates innumerable signal transduction pathways, including ATM, mTOR, and p38 MAPK (Yu et al., *Science* 297: 259-263, 2002; De Giorgi et al., *FASEB J.* 10: 607-609, 2002).

Thus, redox status of roost cellular membranes is rapidly altered by brief exposure to permeant oxidants, and cell death rapidly ensues, through both apoptotic (nuclear) and necrotic (plasma membrane) changes. Membrane-permeant reductants, such as phthalazinediones plus reduced biopterins and thiols, should be able to buffer and maintain the proper redox status in membranes of oxidant-stressed organelles as occurs in acute neurodegenerative syndromes such as hypoxia or glucose deficient states, or in chronic inflammatory states such as Parkinson's disease, Alzheimer's disease, ALS, MS, AT, or aging.

Example 13

Role of Thiol Redox Status in Mitochondrial Activities

The major source of chemical energy and heat in aerobic cells is mitochondria. The modulatable permeable pores and channels in mitochondria are exquisitely sensitive to thiol redox status. The specific mitochondrial channel is composed of two thiol redox sensitive proteins located in the inner membrane—adenine nucleotide translocase (ANT) and voltage dependent anion channel (VDAC)—and other coproteins such as cyclophilin D, hexokinase, benzodiazepine receptors, and the Bcl-2/Bax family of peptides. These proteins together control the permeability and transport of mitochondrial transmembrane channels and pores, which control ADP entry, proton exit, electron flow, intracellular calcium concentration, and $O_2^-$ production.

Bax, benzodiazepine receptors, and hexokinases, which bind to the outer membrane of mitochondria, regulate transport and pore formation in these membranes. Major physiologic modulators of this mitochondrial transmembrane pore include:

(1) transmembrane voltage, which is generated by electron and proton gradients;

(2) inducible membrane proteins, Bcl-2 and Bax; and (3) thiol redox status, the redox state of Cys-56 on the channel protein ANT being a major regulator of the permeability of mitochondrial transmembrane pores (He and Lemasters, *FEBS Letters* 512: 1-7, 2002).

Thiol oxidants or cross-linking agents such as diamide or diethyl maleate distort and open mitochondrial pores and channels, and uncouple electron flow, allowing oxygen to trap electrons and produce $O_2^-$, $H_2O_2$, and other radicals. Energy production declines, and mitochondria release cytochrome c, caspases, and AIF. Destructive cytochrome c, redox-sensitive proteases, and caspases are activated in the cytoplasm and the nucleus, causing cell death, both apoptotic and necrotic.

Reduced thiols, dithiothreatol, glutathione, N-acetyl cysteine, or agents such as Bcl-2, Bongkrekic acid, cyclosporine A, or chaperone cyclophilins that can stabilize ANT sulfhydryls and maintain pore permeability status can completely prevent the electron leak and the cell death (Armstrong and Jones, *FASEB J.* 16: [online], Jun. 7, 2002; Castantini et al., *Oncogene* 19: 307-314, 2000; Hong et al. *FASEB J.* 16: 1633-1636, 2002). Whether permeant reductants such as the phthalazinediones of the present invention, which stabilize and maintain thiol redox status, alone stabilize the thiol redox sensitive mitochondrial transmembrane pore in vivo is currently under investigation.

Under oxidant stressed conditions, including radiation, chemotherapy, occlusive vascular diseases, leptin-deficient or resistin-induced obesity, caloric excesses, and type II diabetes, in which optimal thiol redox status is not maintained by the diseased adipose tissue of the patient, therapeutic support by external thiol redox buffers will be acutely necessary, at least until the patient can repair and buffer the stressed and imbalanced thiol redox status and fully activate its hypoxia-inducible transcription factors (Wenger, *FASEB J.* 16: 1151-1162, 2002; De Giorgi at al., *FASEB J.* 10: 607-609, 2002).

Depending on the type of oxidative stress, labile vicinal cysteinyl residues on ANT undergo cyclic oxidation, ionization, and eventually cross-linking. These oxidations and cross-linkages of protein thiols greatly perturb channel functions, especially by thiol cross-linking cyclic amines, diazenes (diamide), or phenylarsines. Uptake of ADP fails, protons are released with collapse of the inner membrane potential, ordered electron flow at mitochondrial Complex III falters, and $O_2$ now accepts the fluxing electrons with production of $O_2^-$ and other radicals. The oxidant-producing mitochondria release cytochrome c and AIF, and downstream oxidation of $NF_KB$, API (major transcription factor for proliferation), AsK-1 (apoptosis stimulating kinase), glutathione, Bax, HDAC (histone deacetylase in nucleus), PTEN (phosphatase in cytoplasm), and ATM occurs. Apoptosis, senescence, quiescence, or necrosis results, depending largely on the extent and duration of the redox stress.

A photoactive diamine fluorescent cation, tetramethyl-rhodamine, which accumulates in mitochondria and releases free radicals when photoactivated, is a potent agonist of the mitochondrial transmembrane pore. When tetramethyl-rhodamine is activated, all downstream effects of oxidation and cross-linking of ANT's labile cysteinyl residues occur, including translocation and polymerization of Bax in mitochondrial membranes. These effects are fully inhibited by Bongkrekic acid, a specific inhibitor of mitochondrial transmembrane pores (De Giorgi at al., *FASEB J.* 10: 607-609, 2002), as well as by reduced thiols, reduced phthalazines, cyclophilins, and pterines. These observations suggest that the fate of cells under stress is largely dictated by mitochondrial thiol redox status, and that cell fates are readily buffered or controlled by permeant lipophilic redox-sensitive amines, such as phthalazinediones, tetrahydrobiopterin, and permeant thiols.

Example 14

Thiol Redox Status in Mitochondria in Cancer Treatment

Controlling entry and exit of small molecules—$Ca^{2+}$, $H^+$, $O_2^-$ and substrate anions through the redox- and voltage-sensitive mitochondrial channels and pores is to control cell fates. These channels and pores modulate concentrations of intracellular cations $Ca^{2+}$ and $H^+$, intracellular anions ADP, ATP, malate, and glutamate, and intracellular thiols, glutathione, cysteine, thioredoxin, and biopterin. By these means, these channels can indirectly modulate redox-sensitive sites in signal transduction, proliferation, development, transcription, apoptosis pathways, and necrosis pathways, thereby dictating cell fates.

Many agents that can directly modulate these pores are in use for antiproliferative therapies, notably as treatments for hyperproliferative syndromes and cancer (Miccoli et al., *J. Nat. Cancer Inst.* 90: 1401-1406, 1998; Ravagnan et al., *Oncogene* 18: 2537-2546, 1999; Larochette at al., *Exp. Cell Res.* 249: 413-471, 1999). Three broad classes of modulators are in use—lipophilic peptides, lipophilic amines, and thiol redox-reactive cyclic amines.

Lipophilic peptides are useful as antiproliferative and anti-inflammatory therapies. These peptides, primarily Bax, Bcl-2, and cyclosporine A, either block or bypass mitochondrial transmembrane channels by creating pores of oxidized polymerized peptides of variable permeability in the mitochondrial outer membranes (De Giorgi et al., *FASEB J.* 10: 607-609, 2002). The redox-insensitive lipophilic benzo amines are useful in cancer therapy. Diazepam and lonidamine, for example, bind to mitochondrial benzodiazepine receptors in the mitochondrial matrix, block mitochondrial electron flow and ATP synthesis, and induce apoptotic and necrotic death in rapidly growing cells (Miccoli et al., *Nat. Cancer Inst.* 90: 1401-1406, 1998). As for the thiol redox-sensitive cyclic amines, their usefulness in mitochondrial transmembrane pore modulation has not been fully explored.

Diamide (diazenedicarboxylic acid), the thiol cross-linking non-cyclic amine, completely opens mitochondrial transmembrane pores, which causes the mitochondrial transmembrane potential to collapse, with dissipation of $H^+$ (pH) gradients, production of $O_2^-$, and release of the apoptosis inducing factors cytochrome c and AIF. Consequently, cells slowly die depending on their supplies of reduced thiols, primarily glutathione (Zamzami et al., *Oncogene* 16: 1055-1062, 1998). However, although a potent eradicator of cancer cells and other proliferating cells of the subject, this cross-linking non-cyclic amine is too toxic for clinical uses.

Other cyclic lipophilic amines, such as amino phthalazinediones, biopterins, and rhodamines, which accumulate electrostatically in mitochondrial transmembrane pores and accept and release both electrons and protons, reversibly serve as both electron and pH buffers in the polarized channels and pores. In this manner, the ionic and oxidative status of the labile sulfhydryl in ANT is maintained by these redox- and pH-sensitive amines. The cyclic amines thus affect voltage in the channels, and fluxing electrons are either trapped by $O_2$ as $O_2^-$ or proceed downstream with production of $H_2O$ and ATP. At low doses of these compounds, electron flow increases, electrons proceed downstream to $H_2O$, ATP production increases, DNA synthesis and cell proliferation increase, and cell death is aborted. At high doses, electron flow to $H_2O$ decreases, substrate anion translocations falter, membrane potential declines, ATP production ceases, as does electron flow, and cells go into a quiescent $G_0/G1$ phase or apoptosis.

With the lipophilic tetramethyl-rhodamine, many electrons are shunted directly to $O_2$, with the result that $O_2$ accumulates, mitochondrial transmembrane pores open with loss of membrane potential, and apoptotic and necrotic pathways are activated (De Giorgi at al., *FASEB J.* 10: 6076609, 2002). Phthalazinediones, such as amino derivatives, combined with reduced biopterins, thiols, or lipoid acid, modulate electron flow to $O_2^-$ or $H_2O$ (Lynn at al., unpublished). Specifically, at low doses, amino phthalazinediones upregulate the subject's immune responses to eradicate cancerous cells. At high doses, amino phthalazinediones stop proliferation of hyperproliferating cancerous cells. Thus, by upregulating or downregulating particular cells, amino phthalazinediones are useful in cancer treatment (Tzyb et al., *Int. J. Immunorehabilitation* 12:398-403, 1999).

Modulation of mitochondria by these bifunctional cyclic phthalazines is most effective in controlling cell fate in proliferating cells that are deficient in biological thiol redox buffers (Armstrong and Jones, *FASEB J.* 16: [online], Jun. 7, 2002; Larochette at al., *Exp. Cell Res.* 249: 413-471, 1999), or in proliferating cells deficient in cell cycle checkpoint genes (Yan et al., *Genes and Dev.*, in press). Thus, redox- and pH-sensitive amines that buffer by dually modulating mitochondrial transmembrane pores and anion channels are clinically useful both in preventing and treating hyperproliferation states such as cancers.

Example 15

Use of Phthalazinediones in Chronic Dys-Metabolic Syndromes

Food intake, especially fat, with excess deposition of fat in adipose cells causes production and secretion of large amounts of the adipose tissue defense peptide hormones—resistin, leptin, tumor necrosis factor, adiponectin. These collagen- and complement-like peptides facilitate uptake of glucose and combustion of long-chain fatty acids via peroxisome proliferator receptors (PPAR) and mitochondria, with production of heat in the muscle mitochondria, facilitated by activating uncoupling, proteins in mitochondria. This removal of the excess fatty acids relieves the fatty acid-induced stress in adipocytes and also lowers levels of toxic, free fatty acids in blood.

However, in time, with prolonged intake of fatty foods, as in affluent societies, and with consequent excessive storage of fat in adipose cells, these overstuffed fat cells produce and secrete more of the inflammatory cytokines, tumor necrosis factor, and resistin (a redox-sensitive adipokine), at the expense of secretion of adiponectin. In aging individuals with overstuffed fat cells, blood levels of tumor necrosis factor and resistin are high; adiponectin and plasminogen-activator inhibitors are low; glucose, free fatty acids, triglyceride, and insulin are high; and the PPARγ/RXR (retinoid X receptor) complexes in fat and muscle cells are under-activated. Vascular accidents in heart and brain, with atherosclerotic plaques, are also greatly increased in these insulin-resistant individuals. This metabolic syndrome, also called Syndrome X, is epidemic.

Metabolic syndrome is a condition marked by excessive abdominal fat, diabetes, high blood pressure, and cholesterol problems, and is caused by the body's inability to use insulin efficiently, which in turn results from overeating and inactivity. Metabolic syndrome is currently and partially treated with various benzolated thiazolidinediones. These cyclic nitrogenous diketones, which are structurally similar to the phthalazinediones of the present invention, bind to the promoters of PPARγ in the nucleus and activate multiple gene families that activate peroxisomal fatty acid oxidation with increased production of adiponectin and catalase, increased glucose uptake, and increased production of enzymes required for fatty add synthesis and oxidation and for terminal differentiation in adipocytic precursor cells. At high concentrations, these diketone ligands of PPARγ also block proliferation and activities of activated macrophages, endothelial cells, microglia in brain, and probably proliferating smooth muscle cells in atheromatous plaques. Thus, benzolated thiazolidinediones are useful in preventing metabolic syndrome and its downstream sequelae, including insulin resistance, vascular degeneration with hypertension, macrophage proliferation and hyperactivity, with plaque formation and type II diabetes.

Benzolated phthalazinediones chemically resemble benzolated thiazolidinediones and are known to reproduce some functions of benzolated thiazolidinediones, perhaps as a ligand for PPARγ. In particular, amino phthalazinediones, like benzolated thiazolidinediones, also stop proliferation and suppress destructive overactivity by inflammatory and adipose cells, with production of many inflammogens. Whether amino phthalazinediones are actually a ligand for PPARγ, can suppress tumor necrosis factor and resistin secretion in adipocytes and macrophages, and increase secretion of adiponectin by adipocytes are under investigation. Whether benzolated thiazolidinediones, like amino phthalazinediones, can bind to benzodiazepine receptors in mitochondria and alter activity of ion channels and megapores in mitochondria are also not presently known.

Since benzolated thiazolidinediones are very poor redox agents, it is not likely that they directly modulate thiol redox status in mitochondrial voltage-dependent channels or in the permeability pores. In contrast, since amino phthalazinediones probably possess those dual defensive functions, as a redox buffer in mitochondria and as a PPAR activator in the nucleus, amino phthalazinediones promise a better and more complete therapy for all symptoms of metabolic syndrome. Combinational therapy with benzolated thiazolidinediones and amino phthalazinediones, plus thiols and other redox adjuvants, may be the treatment of choice for prevention of downstream sequelae of metabolic syndrome, such as hyperglycemia, hyper fatty acidemia, increased tumor necrosis factor and resistin levels, hypo-adiponectin-emia, hyper or hypo insulin-emia, impaired thiol redox status (hypo-glutathione and cysteine-emia), PPARγ inactivity, and mitochondrial energy uncoupling with elevated $H_2O_2$, $OHOO^-$, and cytoplasmic cytochrome c.

Repeated monitoring of the above adipose hormones during treatments with benzolated thiazolidinediones/amino phthalazinedione/thiol therapies will be required to establish specific dosage and efficacy for each individual. Since with each individual, downstream sequelae of metabolic syndrome, including insulin resistance with long-chain fatty acid poisoning, vary greatly, dose adjustments according to individual responses, as measured by the above adipokine markers, will be required for optimum therapy.

Example 16

Stress-Induced Phosphorylation Signaling and Phthalazinediones

The major survival and growth signaling pathways in some cells involve the phosphorylation of epidermal growth factor receptor (EGFR), mitogen-activated protein kinases (MAPK), extracellular signal-regulated kinases (ERK), phosphoinositol-3 kinase, protein kinase B, and inhibitor $_\kappa$B kinase (IKK), the kinase controlling $NF_\kappa B$ activity, $NF_\kappa B$ being a major stress-induced transcription factor. The cell death pathway is controlled by c-Jun N-terminal kinase (INK), p38, and p53, another stress-induced transcription factor.

Oxidants such as $H_2O_2$ activate intracellular phosphorylation cascades responsible for cell survival and growth and for cell death via apoptosis and necrosis (Wang et al., *J. Biol. Chem.* 275: 14624-1463, 2000). Low doses of $H_2O_2$ directly and rapidly activate the survival pathway, using primarily Akt, PI-3K, EGFR, and $NF_\kappa B$. The apoptotic factors Bad and caspase 9 are also downregulated by low doses of $H_2O_2$. Higher doses of $H_2O$ or prolonged exposure to $H_2O_2$ activate the cell death pathways involving INK, p53, Box, sphingomyelinase, caspases, and the apoptosis signaling kinase AsK-1.

Thus, oxidants, much like the phthalazinediones of the invention, activate either cell survival or cell death pathways, depending on dosage. However, $H_2O_2$ is not a buffer and cannot maintain optimal redox potentials sufficient to maintain cell signaling and growth. $H_2O_2$ also does not scavenge the excess reactive oxygen species produced by activated cell growth pathways. The ability of phthalazinediones, especially amino phthalazinediones, to provide both oxidizing and reducing potential to mitochondria, peroxisomes, and cytoplasmic signaling pathways makes these compounds an ideal in vivo redox buffer capable of dictating most cell fates.

In disease states where signal-induced cell death rates exceed cell growth rates—as in various neurodegenerative syndromes such as Alzheimer's disease, ataxia telangiectasia, Parkinson's disease, multiple system atrophy, or AIDS—or in disease states where autonomous growth signaling rates exceed cell death rates—as in cancers, ataxia telangiectasia, trichothiodystrophy, or hyperinflammatory syndromes—amino phthalazinediones dictate cell fates by buffering the aberrant cellular redox potentials up or down, both in the stressed patient and in any invading or overactivated cell. The phthalazinediones of the invention are likely to be therapeutically useful for modulating aberrant phosphorylation signaling syndromes involved in cell growth and death.

Example 17

Neuronal Overactivity and Amino Phthalazinediones

In Parkinson's disease, neurons of the subthalamic nucleus (STN) become imbalanced and discharge too much. This 4 Hz oscillatory overactivity in STN neurons of patients with the classical symptoms of parkinsonism—bradykinesia, rigidity, and tremor—is a major etiologic factor in Parkinson's disease. Suppression of this oscillatory activity by intra-STN injection of various agents such as lidocaine and muscimol (a gamma aminobutyric acid-A receptor agonist) or chronic electrical (2V) stimulation promptly relieves these parkinsonian symptoms.

The cause of this 4 Hz overactivity in only a few STN neurons is not known (Levy et al., *Brain* 124: 2105-2118, 2001; Luo et al., *Science* 298: 425-429, 2002; Limousin et al., *New England J. of Med.* 339: 1105-1111, 1998; Alvarez et al., *Movement Disorders* 16: 72-78, 2001). The downstream effects of STN overactivity in substantia nigra reticulata, globus pallidus, and motor thalamus are likely to be responsible for multiple movement disorders.

Since maintaining this excessive and imbalanced 4 Hz oscillation requires increased enemy expenditures, agents such as amino phthalazinediones, which can modulate thiol redox status, downregulate mitochondrial energy production, and gain access to the overactivated STN neurons, can potentially suppress the 4 Hz overactivity and thereby suppress and modulate the downstream network activities responsible for the symptoms. Daily intraperitoneal injections of 200 μg of 4-sodium amino phthalazinedione significantly delay the progress of the movement disorder with paralysis induced by MOMU-LV-Ts1 virus in mice. Whether this is due to suppression of oscillatory activity in neurons, suppression of virus-induced astrocytic inflammatory responses, or both is under investigation. Amino phthalazinediones should, however, suppress both the neuronal and astrocytic overactivity.

Example 18

Multiple Chemical Sensitivity Syndrome

Multiple chemical sensitivity (MCS) is a decompensating syndrome in which individuals develop hypersensitivities to multiple environmental toxins, e.g., exhaust fumes from vehicles, factories, garbage dumps, or explosives, perfumes, sulfur oxides, nitrous oxide, and cyclic hydrocarbons produced by molds or plants. Inhalation of such toxins causes symptoms like fatigue, weakness, loss of equilibrium, sensory impairments in smell, taste, hearing, vision, and sensation, cognitive impairments in memory, concentration, and motivation, and motor symptoms that vary from muscle and hone wasting to athetoid, epileptiform, or fibrillary movements. External signs of premature aging, e.g., graying or loss of hair, wrinkling of skin, bradykinesia, or signs of Syndrome X (type II diabetes, hypertension, hyperlipidemia, atrial fibrillation) are usually present at least to some extent.

The multiple incapacitating symptoms of MCS are rapidly induced by inhaling trace amounts of the noxious substance. Removal of the inciting inhalant prevents the acute symptomology but does not eliminate the hypersensitivity. The most characteristic symptom is an inability to "get up and go," or lead a productive life. The symptoms may become permanent or persist for months unless the chronic exposure is eliminated. The inhaled toxins are thought to induce redox imbalances in the naso-olfactory system and brain, and preliminary findings suggest that the functional impairments in MCS are due to acute imbalances in $NO/O_2^-$ and thiol redox potentials in the naso-olfactory system.

Studies also suggest that the neuromuscular and cognitive dysfunctions in MCS may represent redox imbalances in pathways controlling neurotransmission. The constant neurotransmission in neurons, with its repetitive separation of charges, obligatorily produces large amounts of reactive oxygen and nitrogen species. Under stress, these radicals may accumulate with pathologic results. The cell's major redox buffers for controlling these signaling radicals, e.g., reduced thiols such as glutathione, cysteine, and thioredoxins, are rapidly consumed under redox stresses such as anoxia, nutrient or ion deprivation, and aberrant peptide accumulation.

The symptomatic redox imbalances may be corrected by appropriate redox support to the impaired naso-olfactory system. Treatment with thiol redox support, i.e., inhaled or intramuscular glutathione, has been partially successful. Intranasal inhalation of a solution of 25 mg/ml of a phthalazinedione of the invention and 12 mg/ml of sodium glutathione in isotonic NaCl four times per day for three days should remove the incapacitating weakness and the sensory and cognitive symptoms within 48 hours. Inhalation of the reduced phthalazinedione, along with a reduced thiol, can quickly but temporarily rebalance the thiol redox imbalance in the patient's brain and quickly ameliorate some of the symptoms. Motor symptoms may be reversed by prolonged treatment with higher doses of this combined redox therapy.

The foregoing material describes various aspects of the invention and how it may be practiced. The description is not intended to be exhaustive of the many different embodiments of the invention. Although the foregoing invention has been described in some detail by way of illustration and example, to aid understanding, it will be readily apparent to those of ordinary skill in the art, in light of the teachings of this invention, that certain changes and modifications may be made to the invention without departing from the spirit or scope of the appended claims.

What is claimed is:

1. A pharmaceutical composition comprising a phthalazinedione or its pharmaceutically acceptable salt, ester, solvate, hydrate, metabolite, enantiomer, isomer, tautomer, amide, prodrug, or free base; a compound that is an amino acid, antibiotic, antiviral agent, antiinflammatory agent, antioxidant, immunomodulator, reductant, oxidative protector, steroid, or vitamin; and one or more pharmaceutically acceptable excipients,
wherein the phthalazinedione is a alkylaminophthalazinedione, methanoylaminophthalazinedione, ethanoylaminophthalazinedione, propanoylaminophthalazinedione, alkanolaminaphthalazinedione, alkentylaminophthalazinedione, alkoxyaminophthalazinedione, haloalkylaminophthalazinedione, allylaminophthalazinedione, or sulthydrylaminophthalazinedione.

2. The pharmaceutical composition of claim 1, wherein the phthalazinedione is a methylaminophthalazinedione, ethylaminophthalazinedione, propylaminaphthalazinedione, isopropylaminophthalazinedione, methanolaminophthaiazinedione, ethanolaminophthalazinedione, propanolaminophthalazinedione, methenylaminoplathalazinedione, ethenylaminophthalazinedione, propenylaminophthalazinedione, methoxyaminophthalazinedione, ethoxyaminaphthalazinedione, propoxyaminophthalazinedione or dimethylaminophthalazinedione.

3. The pharmaceutical composition of claim 1, wherein the phthalazinedione is 6-amino-2,3-dihydrophthalazine-1, 4-dione, or 5-amino-2,3-dihydroplathalazine-1,4-dion-8-yl.

4. The pharmaceutical composition of claim 2, wherein the phthalazinedione is N-methyl-5-amino-2,3-dihydrophthalazine-1,4-dione, N-ethyl-5-amino-2,3-dihydrophthalazine-1,4-dione, N-propyl-5-amino-2,3-dihydrophthalazine-1,4-dione, N-isopropyl-5-amino-2,3-dihydrophthalazine-1,4-dione, N-methanoyl-5-amino-2,3-dihydrophthalazine-1,4-dione, N-ethanoyl-5-amino-2,3-dihydrophthalazine-1,4-dione, N-propanoyl-5-amino-2,3-dihydrophthalazine-1,4-dione, N-methanol-5-amino-2,3-dihydroplathaiazine-1,4-dione, N-ethanol-5-amino-2,3-dihydrophthalazine-1,4-dione, N-propanol-5-amino-2,3-dihydrophthalazine-1,4-dione, N-methenyl-5-amino-2,3-dihydrophthalazine-1,4-dione, N-ethenyl-5-amino-2,3-dihydrophthalazine-1,4-dione, N-propenyl-5-amino-2,3-dihydrophthalazine-1,4-dione, N-methoxy-5-amino-2,3-dihydrophthalazine-1,4-dione, N-ethoxy-5-amino-2,3-dihydrophthalazine-1,4-dione, N-propoxy-5-amino-2,3-dihydrophthalazine-1,4-dione, N,N-dimethyl-5-amino-2,3-dihydrophthalazine-1,4-dione, N-acetylcysteine-5-amino-2,3-dihydrophthalazine-1,4-dione, or N-acetylglutathione-5-amino-2,3-dihydrophthalazine-1,4-dione.

5. The pharmaceutical composition of claim 1, wherein the compound is a glutathione, glucocorticoid, dexamethasone, cysteine, lipoic acid, biopterin, hydralazine, rasagiline, thioredoxin, ferulic acid, minocycline, menadione, tetracycline, isosorbate dinitrate, dextromethorphan, dithiothreitol carnosine, or clomethiazole.

6. The pharmaceutical composition of claim 1, wherein the composition is in a pharmaceutically acceptable form selected from the group consisting of tablet, capsule, granule, powder, solution, suspension, microsphere, liposome, colloid, lyophilized composition, gel, lotion, ointment, cream, spray, and suppository.

7. The pharmaceutical composition of claim 4, wherein the phthalazinedione is N-methyl-5-amino-2,3-dihydrophthalazine-1,4-dione or N-ethanoyl-5-amino-2,3-dihydrophthalazine-1,4-dione.

* * * * *